(12) United States Patent
Till

(10) Patent No.: US 7,703,262 B2
(45) Date of Patent: Apr. 27, 2010

(54) BEVERAGE BOTTLING PLANT FOR FILLING BOTTLES WITH A LIQUID BEVERAGE MATERIAL HAVING A DEVICE TO TREAT BOTTLES AND A METHOD OF TREATING BOTTLES WITH SAID DEVICE

(75) Inventor: Volker Till, Hofheim/Taunus (DE)

(73) Assignee: KHS Maschinen- und Anlagenbau AG, Dortmund (DE)

( * ) Notice: Subject to any disclaimer, the term of this patent is extended or adjusted under 35 U.S.C. 154(b) by 570 days.

(21) Appl. No.: 11/175,118

(22) Filed: Jul. 5, 2005

(65) Prior Publication Data

US 2006/0011263 A1    Jan. 19, 2006

(30) Foreign Application Priority Data

Jul. 7, 2004    (DE) ................. 10 2004 032 861

(51) Int. Cl.
    *B65B 55/08*    (2006.01)
    *A61L 2/10*    (2006.01)

(52) U.S. Cl. .................. 53/426; 53/167; 250/455.11; 422/24

(58) Field of Classification Search ............... 53/253, 53/331.5, 317, 319, 426, 167; 422/24; 250/453.11, 250/454.11, 455.11; *A61L 2/10; B65B 55/08*
See application file for complete search history.

(56) References Cited

U.S. PATENT DOCUMENTS

| | | | |
|---|---|---|---|
| 1,788,906 A * | 1/1931 | Brown .................... | 250/453.11 |
| 2,175,682 A | 10/1939 | Chaffee | |
| 2,194,463 A * | 3/1940 | Powley .................. | 250/453.11 |
| 2,384,778 A | 9/1945 | Whitman | |
| 4,504,114 A * | 3/1985 | Arrington .................... | 385/142 |
| 5,398,734 A * | 3/1995 | Hartel .......................... | 141/83 |
| 5,713,403 A * | 2/1998 | Clusserath et al. .......... | 141/101 |
| 5,768,853 A | 6/1998 | Bushnell et al. | |
| 5,857,309 A * | 1/1999 | Cicha et al. .................... | 53/167 |
| 5,958,336 A | 9/1999 | Duarte | |
| 6,012,267 A * | 1/2000 | Katsumata .................... | 53/425 |
| 6,185,910 B1* | 2/2001 | Achhammer ................. | 53/426 |
| 6,276,113 B1* | 8/2001 | Bernhard ..................... | 53/253 |

(Continued)

FOREIGN PATENT DOCUMENTS

DE    44 07 183 A1    9/1995

(Continued)

OTHER PUBLICATIONS

Machine translation of JP 9-99921 A, from JPO website, http://www4.ipdl.inpit.go.jp/Tokujitu/tjsogodbenk.ipdl, 8 pages Jan. 16, 2009.*

(Continued)

*Primary Examiner*—Stephen F Gerrity
(74) *Attorney, Agent, or Firm*—Nils H. Ljungman & Associates

(57) ABSTRACT

A beverage bottling or container filling plant for filling bottles or containers with a liquid beverage material having a device which utilizes an ultraviolet source to treat the surfaces of the bottles or containers, and a method of treating the surfaces of bottles or containers with the ultraviolet source of the device.

5 Claims, 7 Drawing Sheets

U.S. PATENT DOCUMENTS

| | | | |
|---|---|---|---|
| 6,368,554 B1 * | 4/2002 | Wajsfelner et al. | 250/453.11 |
| 6,517,776 B1 * | 2/2003 | Rodgers et al. | 422/24 |
| 6,536,188 B1 * | 3/2003 | Taggart | 53/426 |
| 6,868,873 B2 * | 3/2005 | Frisk | 141/11 |
| 2006/0140558 A1 * | 6/2006 | Michaloski | 385/115 |

FOREIGN PATENT DOCUMENTS

| | | | |
|---|---|---|---|
| DE | 19909826 A1 * | 9/2000 | |
| EP | 277505 A1 * | 8/1988 | |
| EP | 1046585 A | 10/2000 | |
| EP | 1120121 A2 * | 8/2001 | |
| EP | 0 579 679 B1 | 1/2002 | |
| JP | 63281936 A * | 11/1988 | |
| JP | 06191521 A * | 7/1994 | |
| JP | 09099921 A * | 4/1997 | |
| JP | 2000313075 A * | 11/2000 | |
| JP | 2001247108 A * | 9/2001 | |
| WO | WO 02/36437 A1 | 5/2002 | |

OTHER PUBLICATIONS

European Patent Office Search Report EP05011277 and English translation thereof.

* cited by examiner

BEVERAGE BOTTLING PLANT FOR FILLING BOTTLES WITH A LIQUID BEVERAGE MATERIAL HAVING A DEVICE TO TREAT BOTTLES AND A METHOD OF TREATING BOTTLES WITH SAID DEVICE

BACKGROUND

1. Technical Field

The present application relates to a beverage bottling plant for filling bottles with a liquid beverage material having a device to treat bottles and a method of treating bottles with said device.

2. Background Information

A beverage bottling plant for filling bottles with a liquid beverage filling material can possibly comprise a beverage filling machine with a plurality of beverage filling positions, each beverage filling position having a beverage filling device for filling bottles with liquid beverage filling material. The filling devices may have an apparatus designed to introduce a predetermined volume of liquid beverage filling material into the interior of bottles to a substantially predetermined level of liquid beverage filling material. The apparatus designed to introduce a predetermined flow of liquid beverage filling material further comprises an apparatus that is designed to terminate the filling of the beverage bottles upon the liquid beverage filling material reaching the predetermined level in bottles. There may also be provided a conveyer arrangement that is designed to move bottles, for example, from an inspecting machine to the filling machine. Upon filling, a closing station closes the filled bottles. There may further be provided a conveyer arrangement configured to transfer filled bottles from the filling machine to the closing station. Bottles may be labeled in a labeling station, the labeling station having a conveyer arrangement to receive bottles and to output bottles. The closing station and the labeling station may be connected by a corresponding conveyer arrangement.

The treatment of containers, in particular of containers and/or packaging for perishable contents, such as beverages, cosmetics etc., for example, with ultraviolet radiation is basically known from the prior art (DE 44 07 183 A1, U.S. Pat. No. 2,384,778 and WO 02/36437).

One feature that all the devices and methods of the prior art have in common is that for the emission of the ultraviolet radiation during the sterilization of the interior of the containers, the ultraviolet source is introduced into the respective container through the container opening. At least one of the disadvantages that has to be taken into consideration is the fact that the type and shape of the containers to be sterilized must also be taken into consideration in the realization of the ultraviolet source, and in particular the cross section of the container opening. In other words, the design and construction of the ultraviolet source cannot be based exclusively on the maximum possible radiation generation and the maximum possible efficiency.

The prior art also teaches a method in which, for the internal sterilization of containers, the interior surface of which is to be treated with an ultraviolet radiation generated in an ultraviolet laser that is outside the respective container and simultaneously with an infrared radiation that is also generated in a laser (EP 0 579 679 B1). The radiation is introduced into the individual container by means of reflectors.

OBJECT OR OBJECTS

The object is to indicate a method that makes possible the treatment of the interior of containers and/or packages with ultraviolet radiation in a particularly simple and safe manner. The present application teaches the method and device for the performance of the method herein below.

SUMMARY

The unique feature of the present application is that the emission of the ultraviolet radiation, which is generated by an ultraviolet source that is located outside the respective container, takes place inside the container by means of a flexible optical waveguide element that is introduced into the container via the container opening. The term "container" as used by the present application includes bottles, among other types of containers, as well as packaging that is fabricated from flat material, such as packages for beverages and other liquid foods, for example.

Developments of the present application are described in the dependent claims. The present application is explained in greater detail below with reference to one exemplary embodiment which is illustrated in the accompanying figures.

The above-discussed embodiments of the present invention will be described further hereinbelow. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

DESCRIPTION OF EMBODIMENT OR EMBODIMENTS

Figure 1:
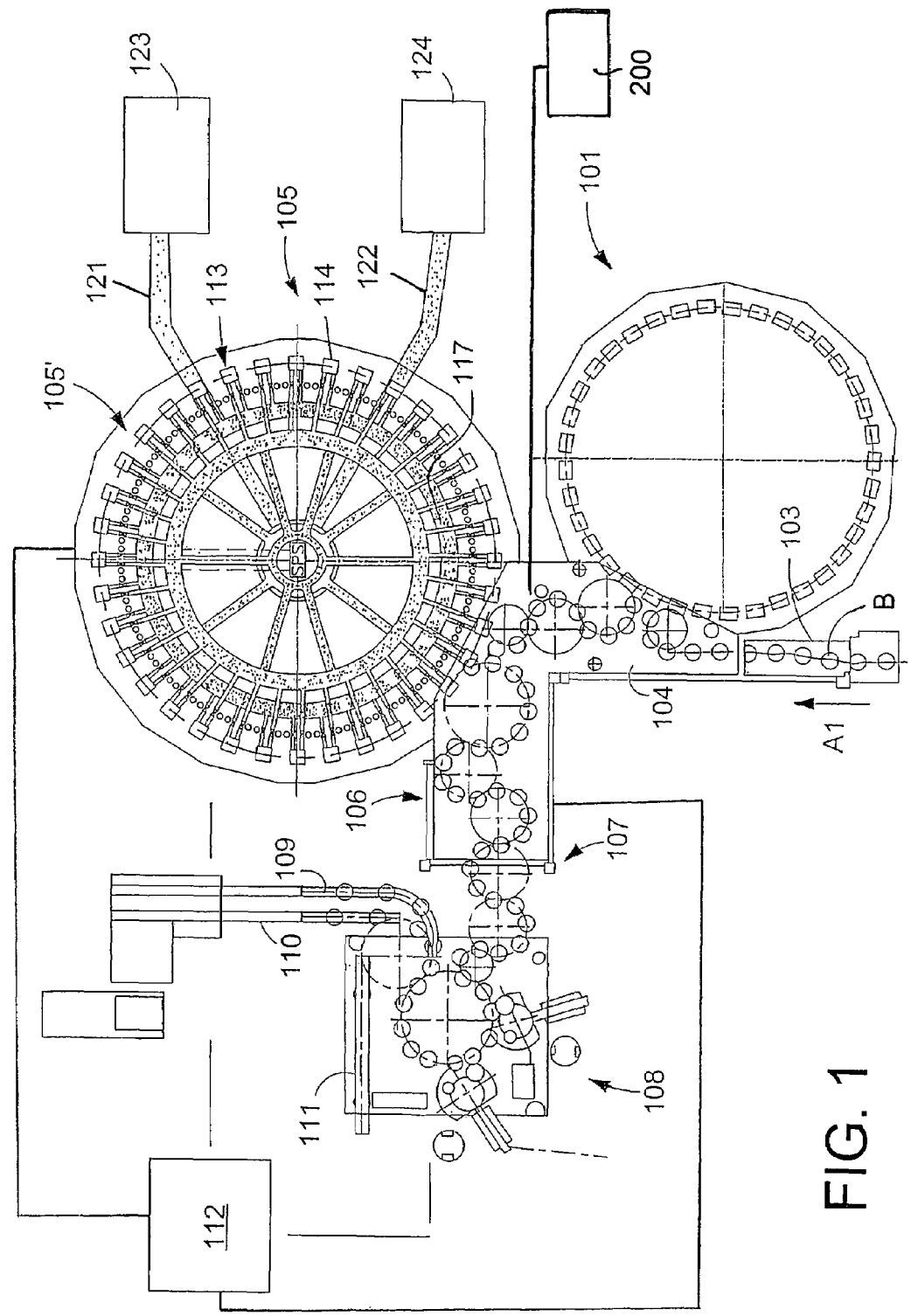
FIG. 1 is a schematic illustration of a container filling plant in accordance with one possible embodiment.

FIG. 1 shows schematically the main components of one possible embodiment example of a system for filling containers, specifically, a beverage bottling plant for filling bottles B with at least one liquid beverage, in accordance with at least one possible embodiment, in which system or plant could possibly be utilized at least one aspect, or several aspects, of the embodiments disclosed herein.

FIG. 1 shows a rinsing arrangement or rinsing station 101, to which the containers, namely bottles B, are fed in the direction of travel as indicated by the arrow A1, by a first conveyer arrangement 103, which can be a linear conveyor or a combination of a linear conveyor and a starwheel. Downstream of the rinsing arrangement or rinsing station 101, in the direction of travel as indicated by the arrow A1, the rinsed bottles B are transported to a beverage filling machine 105 by a second conveyer arrangement 104 that is formed, for example, by one or more starwheels that introduce bottles B into the beverage filling machine 105.

The beverage filling machine 105 shown is of a revolving or rotary design, with a rotor 105', which revolves around a central, vertical machine axis. The rotor 105' is designed to receive and hold the bottles B for filling at a plurality of filling positions 113 located about the periphery of the rotor 105'. At each of the filling positions 103 is located a filling arrangement 114 having at least one filling device, element, apparatus, or valve. The filling arrangements 114 are designed to introduce a predetermined volume or amount of liquid beverage into the interior of the bottles B to a predetermined or desired level.

The filling arrangements 114 receive the liquid beverage material from a toroidal or annular vessel 117, in which a supply of liquid beverage material is stored under pressure by a gas. The toroidal vessel 117 is a component, for example, of the revolving rotor 105'. The toroidal vessel 117 can be connected by means of a rotary coupling or a coupling that permits rotation. The toroidal vessel 117 is also connected to at least one external reservoir or supply of liquid beverage material by a conduit or supply line. In the embodiment shown in FIG. 1, there are two external supply reservoirs 123 and 124, each of which is configured to store either the same liquid beverage product or different products. These reservoirs 123, 124 are connected to the toroidal or annular vessel 117 by corresponding supply lines, conduits, or arrangements 121 and 122. The external supply reservoirs 123, 124 could be in the form of simple storage tanks, or in the form of liquid beverage product mixers, in at least one possible embodiment.

As well as the more typical filling machines having one toroidal vessel, it is possible that in at least one possible embodiment there could be a second toroidal or annular vessel which contains a second product. In this case, each filling arrangement 114 could be connected by separate connections to each of the two toroidal vessels and have two individually-controllable fluid or control valves, so that in each bottle B, the first product or the second product can be filled by means of an appropriate control of the filling product or fluid valves.

Downstream of the beverage filling machine 105, in the direction of travel of the bottles B, there can be a beverage bottle closing arrangement or closing station 106 which closes or caps the bottles B. The beverage bottle closing arrangement or closing station 106 can be connected by a third conveyer arrangement 107 to a beverage bottle labeling arrangement or labeling station 108. The third conveyor arrangement may be formed, for example, by a plurality of starwheels, or may also include a linear conveyor device.

In the illustrated embodiment, the beverage bottle labeling arrangement or labeling station 108 has at least one labeling unit, device, or module, for applying labels to bottles B. In the embodiment shown, the labeling arrangement 108 has three output conveyer arrangement: a first output conveyer arrangement 109, a second output conveyer arrangement 110, and a third output conveyer arrangement 111, all of which convey filled, closed, and labeled bottles B to different locations.

The first output conveyer arrangement 109, in the embodiment shown, is designed to convey bottles B that are filled with a first type of liquid beverage supplied by, for example, the supply reservoir 123. The second output conveyer arrangement 110, in the embodiment shown, is designed to convey bottles B that are filled with a second type of liquid beverage supplied by, for example, the supply reservoir 124. The third output conveyer arrangement 111, in the embodiment shown, is designed to convey incorrectly labeled bottles B. To further explain, the labeling arrangement 108 can comprise at least one beverage bottle inspection or monitoring device that inspects or monitors the location of labels on the bottles B to determine if the labels have been correctly placed or aligned on the bottles B. The third output conveyer arrangement 111 removes any bottles B which have been incorrectly labeled as determined by the inspecting device.

The beverage bottling plant can be controlled by a central control arrangement 112, which could be, for example, computerized control system that monitors and controls the operation of the various stations and mechanisms of the beverage bottling plant.

FIG. 1 further shows a treatment or sterilization station, represented by a box 200, disposed between the bottle cleaning machine 101 and the bottle filling machine 105.

Figure 5:
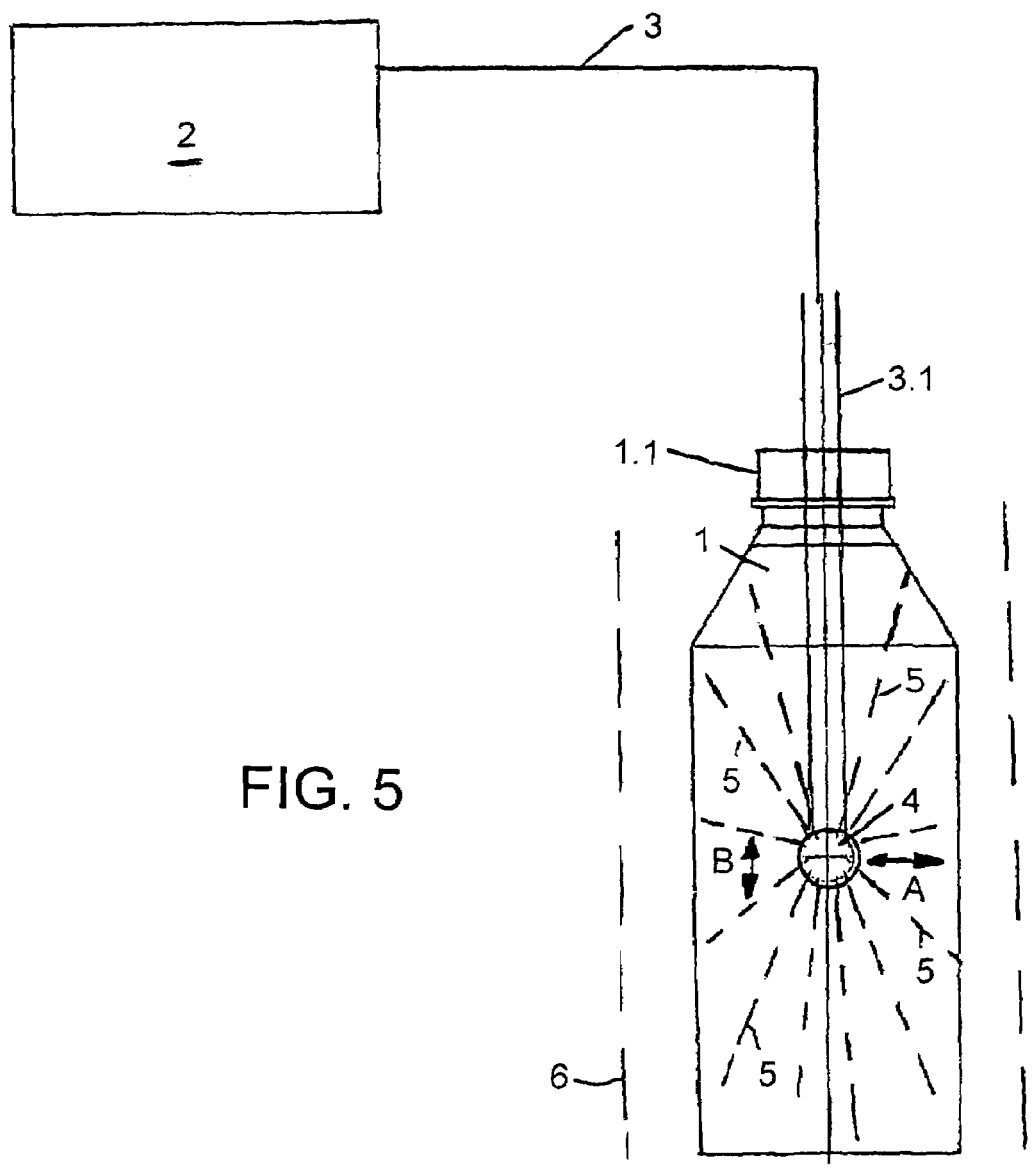
FIG. 5 shows a package or a container for a perishable liquid or highly viscous product, such as a beverage, for example.

FIG. 5 shows a package or a container for a perishable liquid or highly viscous product, such as a beverage, for example. According to FIG. 5, reference numeral 1 refers to a container; reference numeral 1.1 refers to a container mouth; reference numeral 2 refers to an ultraviolet source; reference numeral 3 refers to an optical waveguide element; reference numeral 3.1 refers to a segment of the optical waveguide element; reference numeral 4 refers to an optical element for the three-dimensional emission of the ultraviolet radiation; reference numeral 5 refers to ultraviolet radiation; reference numeral 6 refers to a processing position; and Arrow A, Arrow B refer to relative movement between the optical waveguide 3 or the emitter element 4 and the container 1.

Before the container or package is filled with the liquid, the interior of the container 1 is sterilized by means of ultraviolet radiation in a wavelength range (e.g. 254 nm) that achieves an optimal extermination of the germs and micro-organisms that are on the interior surface of the container. The ultraviolet radiation is produced by a suitable radiation source 2, for example a mercury vapor discharge lamp, an ultraviolet laser or a similar source that has a sufficiently high output. The radiation source 2 is introduced into the container via a flexible optical waveguide element 3. For this purpose, the optical waveguide element 3 is introduced by means of a segment 3.1 through the mouth opening 1.1 into the interior of the container, where it is provided with an optical emitter element 4 that makes possible a three-dimensional, i.e. a spherical emission of the ultraviolet radiation, for example, with an aperture angle of three hundred sixty degrees or almost three hundred sixty degrees in every spatial plane of the space, so that the entire interior surface of the container 1 is covered by the ultraviolet radiation as illustrated by the lines or force or arrows 5. For example, with a special configuration and/or shape of the container 1, to prevent the shadowing of areas on the interior surface of the container that are not covered by the ultraviolet radiation, it is possible to move the end of the optical waveguide element 3 that is introduced into the container 1 relative to the container 1, as indicated with the double-ended arrows A and B in the figure. This movement is easily possible as a result of the flexible configuration of the optical waveguide element.

It is also possible to realize the emitter element 4 so that the direction of radiation can be varied in a controlled manner during the sterilization process, whereby the ultraviolet radiation is emitted preferably not spherically but, for example, radially from a ring-shaped emission aperture that extends over the entire periphery of the emitter element 4, whereby the exit angle of the radiation can be varied in a controlled manner. Micro-mirrors that can be moved by piezoelectric elements, for example, are particularly suitable for the realization of this function.

An additional and altogether advantageous development of this embodiment teaches that the emitter element 4 is realized so that the intensity of the ultraviolet radiation that is emitted in a spherical pattern is not distributed uniformly over the surface of the imaginary sphere but non-uniformly. One advantage of this method is that with an unchanged or even reduced output of the ultraviolet source, critical areas of the container can be irradiated particularly intensively. To realize the radiation intensity so that it is not uniform over the surface, it is appropriate, for example, to position the outlet apertures of the radiation not in a regular pattern, but as required to meet the intensity requirements.

The optical waveguide element 3 comprises, for example, a bundle of optical fibers, whereby these fibers can be made of glass, for example, or another material that is suitable for the manufacture of optical waveguides.

In one practical realization, the ultraviolet sterilization of the interior of the container 1 is performed in a sterilizer that is positioned in a production line upstream of the corresponding filling machine, and which forms a plurality of container receptacles 6, for example, on a rotor that is driven in rotation around a vertical machine axis, to each of which receptacles 6 the containers 1 to be sterilized are fed at a container input, and are then removed from the rotor at a container output, and are transported to the downstream filling machine. Each receptacle 6 thereby has the optical waveguide end 3.1 that is provided with the optical system 4, which for the sterilization process is then introduced in a controlled manner into the interior of the container 1, and after the treatment with the ultraviolet radiation is removed from the container 1 in question, and specifically, for example, by the corresponding raising and lowering of the container 1. Each receptacle 6 is associated, for example, with an independent ultraviolet source 2. Basically, it is also possible to provide a common ultraviolet source 2 for all the receptacles or a common ultraviolet source for a group comprising a plurality of receptacles.

The realization taught by the present application has numerous advantages. As a result of the flexible optical waveguide element 3, as noted above, a relative movement between the end that has the emitter element 4 and the container 1 is possible to eliminate any areas that are not covered by the ultraviolet radiation. As a result of the flexible realization of the optical waveguide element 3, it is also possible to position, install and to move the optical waveguide element 3 in optimal fashion inside the machine (sterilizer). A further advantage is the fact that the flexible optical waveguide element can also follow the movements of the respective container with little mechanical effort. The ultraviolet radiation is reliably conducted in the optical waveguide element and shielding can easily be provided to eliminate the risk of injury.

Because the optical waveguide element 3 can be realized so that it has a small outside diameter, this element can also be introduced into containers that have only a small diameter at the container mouth. In addition, as a result of the realization taught by the present application, the respective ultraviolet source 2 can have almost any desired shape, i.e. the design and construction of this radiation source can be selected, for example, from the point of view of the optimum generation of ultraviolet radiation with the highest possible efficiency, and specifically completely independently of the special type and/or shape of the container 1 to be sterilized.

The embodiments are suitable for the internal sterilization of containers of all types, in particular including for the internal sterilization of containers or packages made of plastic and/or flat material.

Figure 2:
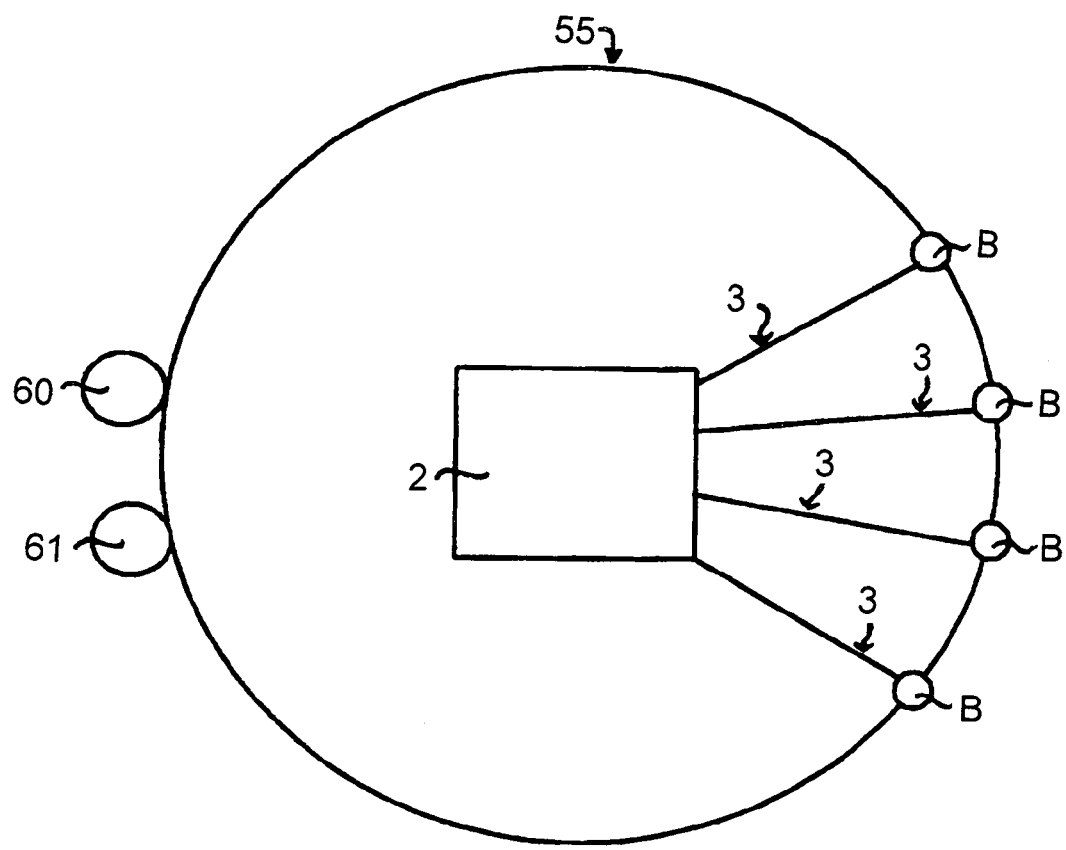
FIG. 2 shows a treatment machine according to one possible embodiment.

FIG. 2 shows the treatment machine according to one possible embodiment. According to FIG. 2, the ultraviolet source 2 has a plurality of optical waveguide elements 3. It should be noted that FIG. 2 shows only four optical waveguide elements 3 for purposes of illustration, and it should be understood that any reasonable number of optical waveguide elements 3 could be placed about the entire periphery of the ultraviolet source 2 in order to efficiently and quickly treat the bottles. A rotor or starwheel 55 is disposed about the ultraviolet source 2, such that the optical waveguide elements 3 project from the ultraviolet source 2 and towards bottles B on the starwheel or rotor 55. An input starwheel 60 and an output starwheel 61 are disposed adjacent the starwheel or rotor 55. The input starwheel 60 feeds bottles B to be treated onto the starwheel or rotor 55, and the output starwheel 61 removes the bottles B from the starwheel or rotor 55 after the bottles B have been treated.

Figure 3:
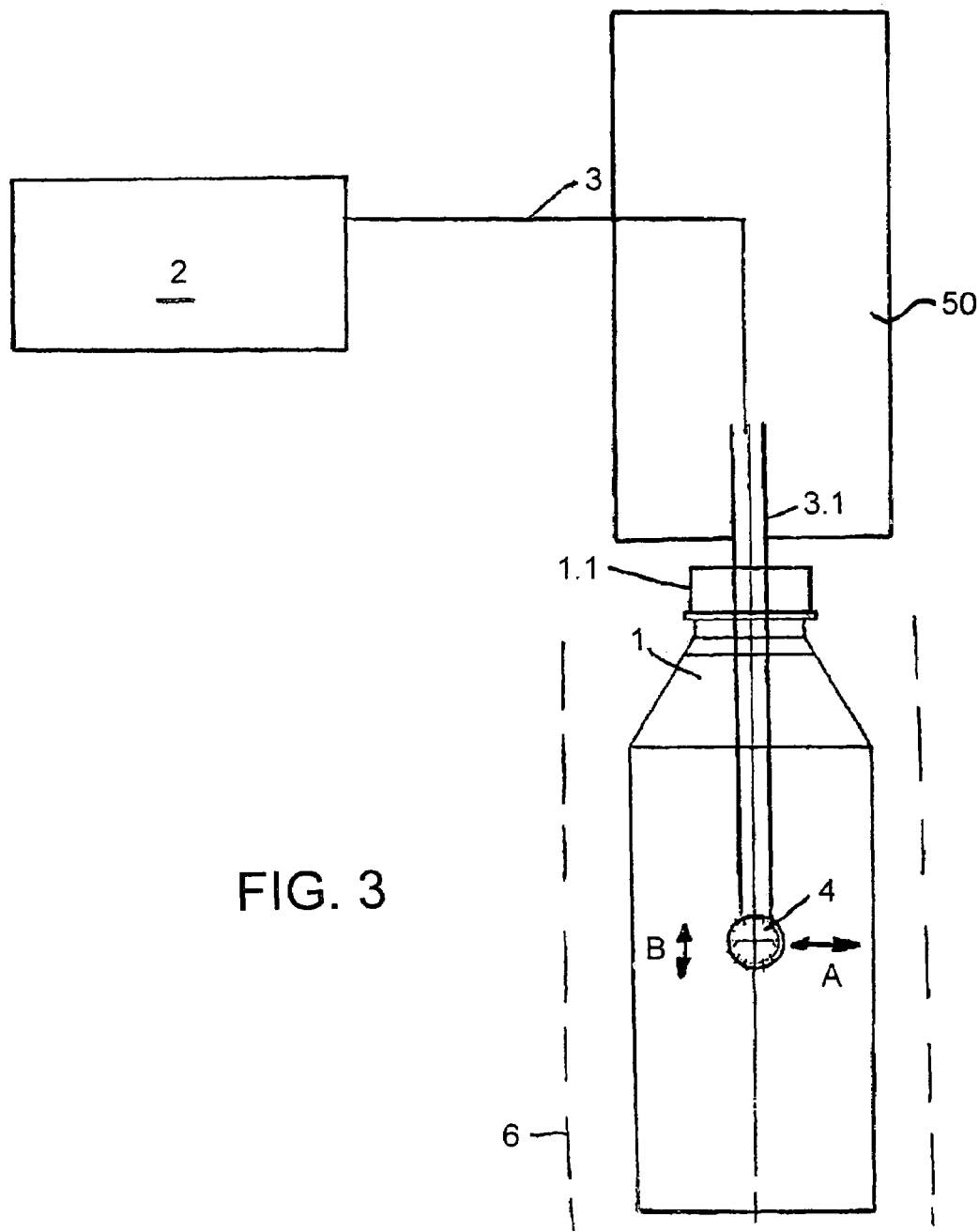
FIG. 3 shows a package or a container, such as for a beverage, and a device for treating the package or container, according to one possible embodiment.

FIG. 3 shows a package or a container 1, such as for a beverage, and a device for treating the package or container 1 according to one possible embodiment. In this embodiment the optical waveguide element 3 is introduced into the container 1, such as a bottle, by a movement apparatus 50, which movement apparatus 50 is represented in FIG. 3 by a box. The movement apparatus 50 could comprise any sort of suitable moving apparatus, such as a cam structure, a pneumatic structure, or a hydraulic structure. The movement apparatus 50 is designed to move the emitter element 4 and the end 3.1 of the optical waveguide element 3 into the container 1 to permit treatment of the container 1, and also to move the end 3.1 and the emitter element 4 of the optical waveguide element 3 out of the container 1 after the container 1 has been treated. In addition, the movement apparatus 50 is designed to adjust or change the position of the end 3.1 of the optical waveguide element 3 and the emitter element 4 inside the container by moving the end 3.1. The adjustment movement can be performed in both the A and B directions, i.e. both vertically and horizontally, so as to treat the interior of the container 1 thoroughly and efficiently, especially if the container or containers 1 to be treated are of various or unusual shapes and/or sizes.

Figure 4:
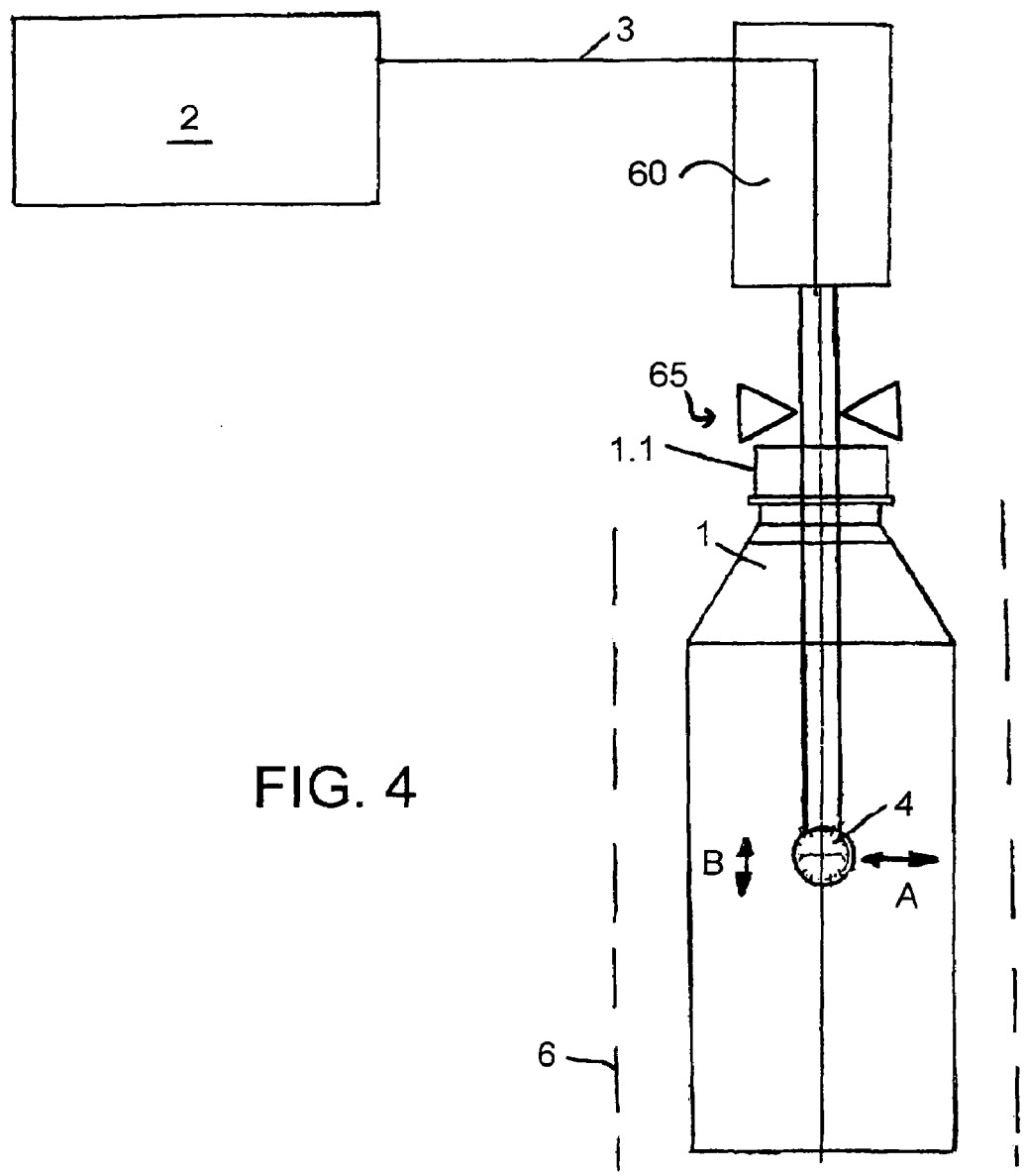
FIG. 4 is similar to FIG. 3, and shows further details according to one possible embodiment.

FIG. 4 is similar to FIG. 3, and shows further details according to one possible embodiment. In this possible embodiment, a fulcrum structure 65 or other similar adjusting mechanism is used to pivot, swing, or move the end 3.1 and the emitter element 4 of the optical waveguide element 3 in the horizontal or lateral direction A inside of the container 1. The additional movement of the end 3.1 of the optical waveguide element 3 inside of the container 1 helps in ensuring that essentially all areas of the container are fully and properly treated, as discussed above. In such an embodiment, the optical waveguide element 3 could be bent to move around the emitter element 4 to produce a pattern of ultraviolet light that would cover essentially all of the inside surfaces of the container 1 to be treated. In the embodiment shown in FIG. 4, a movement apparatus 60, which comprises a solenoid or other drive mechanism and is separate from the fulcrum structure 65, is used to move the end 3.1 and the emitter element 4 in the vertical direction B into the container 1 prior to treatment, and out of the container 1 after the completion of treatment.

Figure 6:
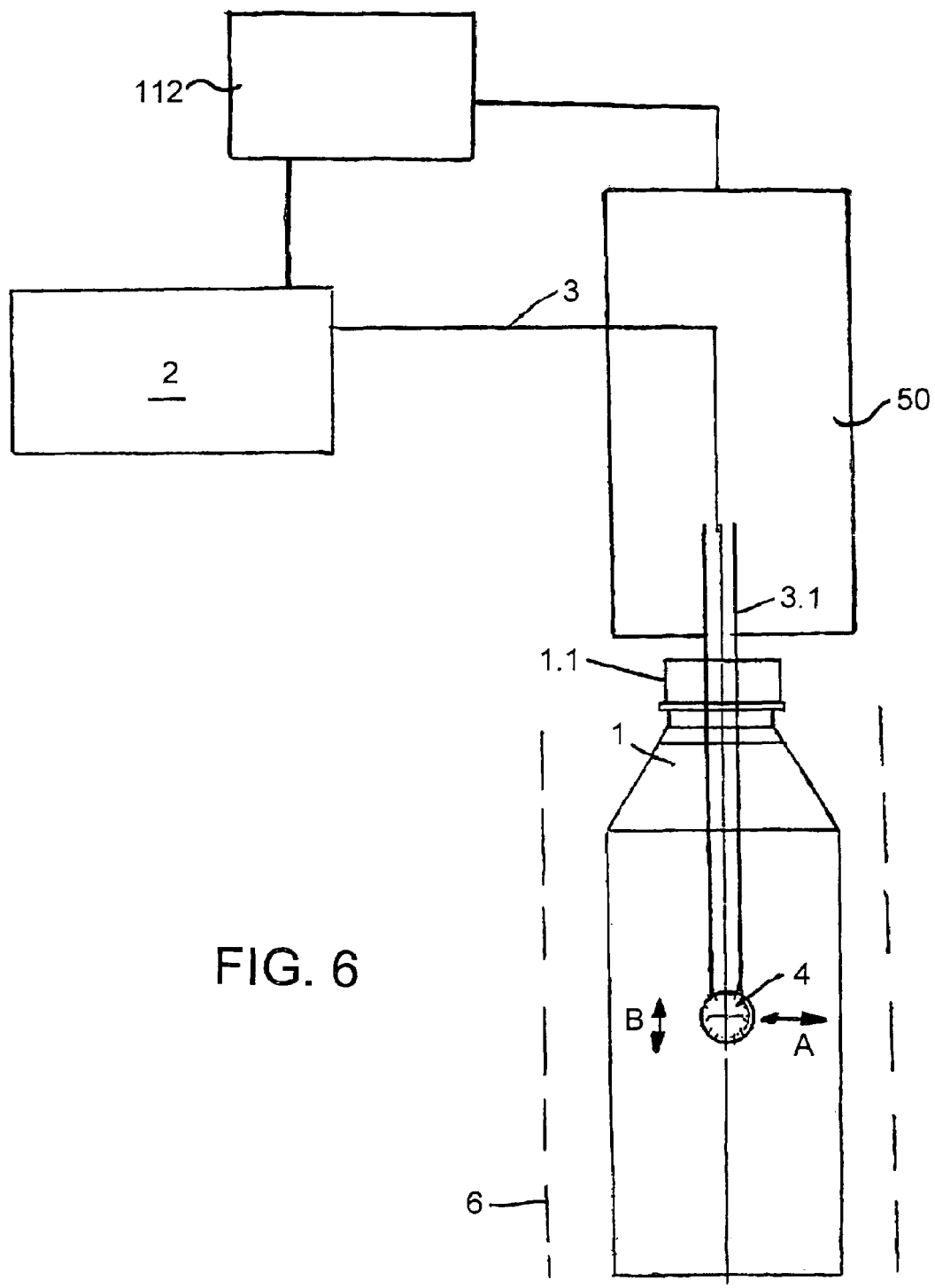
FIG. 6 is similar to FIG. 5, and shows further details according to one possible embodiment.

FIG. 6 is similar to FIG. 3, and shows further details according to one possible embodiment. In this possible embodiment, a central control arrangement 112, such as a computer control system, is used to monitor and control the operation of the treatment station. The central control arrangement 112 further operates the movement apparatus or device 50.

Figure 7:
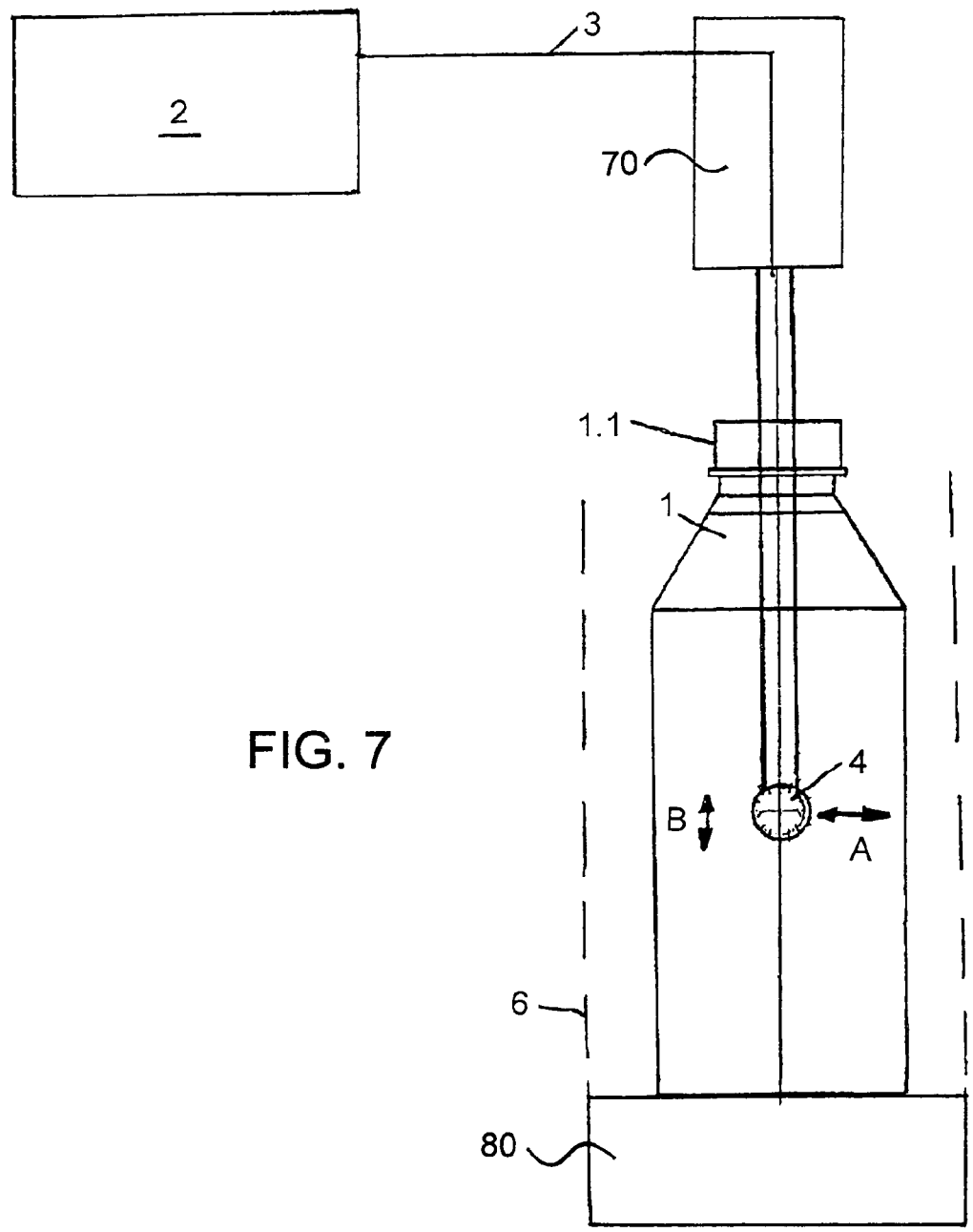
FIG. 7 shows a view of a treatment machine according to another possible embodiment.

FIG. 7 shows another possible embodiment, in which the receptacle 6 comprises or is connected to a support table structure 80, such as are well known in filling machines, capping machines, and labeling machines of the prior art. The support table structure 80 has a drive mechanism (not shown in detail) which permits up and down or vertical movement of the support table structure 80 and the receptacle 6. In this embodiment, the optical waveguide element 3 is stationary with respect to the support table structure 80, and thus the upward movement of the support table structure 80 positions the container 1 about the end 3.1 and the emitter element 4 of the optical waveguide element 3. The emitter element 4 is therefore positioned in the interior of the container 1 as shown in FIG. 7 to permit treatment of the interior of the container 1. In this particular embodiment, an adjusting or movement apparatus 70 is used to produce an adjusting movement of the emitter element 4 in the A and B directions inside the container 1 in order to thoroughly treat essentially the entirety of the inside of the container 1, as discussed above with respect to the other embodiments. After treatment of the container 1 has been completed, the support table structure 80 moves downward and moves the container 1 away from the optical waveguide element 3, thereby producing a relative movement of the optical waveguide element 3 and the emitter element 4 out of the container 1.

It should be understood that the above discussed embodiments and the components thereof could be interchanged or modified as necessary to produce alternative embodiments not specifically disclosed herein and within the scope of the application.

The present application relates to a method for the sterilization of containers, wherein the interior surface of the container is treated with ultraviolet radiation from a ultraviolet source that is emitted in the interior of the container. The ultraviolet radiation from the ultraviolet source, which is located in its entirety outside the container, is emitted via an optical waveguide element that is introduced through the mouth of the container into the interior of the container.

An example of a fiber optic bundle which could possibly be used as waveguides which may possibly be utilized or adapted for use in at least one possible embodiment may possibly be found in U.S. Pat. No. 6,418,254, entitled "Fiberoptic display," issued on Jul. 9, 2002, to Shikata, et al.

An example of a treatment machine for treating bottles, components of which may possibly be utilized or adapted for use in at least one possible embodiment may possibly be found in Germany Patent Application No. 10 2004 030 957.4, filed on Jun. 26, 2004, having inventor Volker Till, and its corresponding U.S. patent application Ser. No. 11/167,077, filed on Jun. 24, 2005, now issued as U.S. Pat. No. 7,497,237 on Mar. 3, 2009.

Some examples of adaptive or deformable mirrors which may possibly be utilized or adapted for use in at least one possible embodiment may possibly be found in the following U.S. Patents: U.S. Pat. No. 6,902,281, entitled "Adaptive optic mirror," having issue date Jun. 7, 2005, and U.S. Pat. No. 6,293,680, entitled "Electromagnetically controlled deformable mirror," having issue date Sep. 25, 2001.

One feature or aspect of an embodiment is believed at the time of the filing of this patent application to possibly reside broadly in a method for the sterilization of containers in which the interior surface of the container is treated with ultraviolet radiation from an ultraviolet source that is emitted in the interior of the container, characterized by the fact that the ultraviolet radiation from the ultraviolet source, which is located in its entirety outside the container, is emitted via an optical waveguide element that is introduced through the container mouth into the interior of the container.

Another feature or aspect of an embodiment is believed at the time of the filing of this patent application to possibly reside broadly in a method, characterized by the use of a flexible optical waveguide element.

Yet another feature or aspect of an embodiment is believed at the time of the filing of this patent application to possibly reside broadly in a method, characterized by the use of an optical waveguide element which is realized on its end that is introduced into the respective container interior for an emission of the ultraviolet radiation via a three-dimensional aperture angle of three hundred sixty degrees or approximately three hundred sixty degrees in every spatial plane.

Still another feature or aspect of an embodiment is believed at the time of the filing of this patent application to possibly reside broadly in a method, characterized by the use of an optical waveguide element which is realized on its end that is introduced into the respective container interior for a ring-shaped emission of the ultraviolet radiation over a three-dimensional aperture angle of three hundred sixty degrees, whereby the exit angle of the ultraviolet radiation can be varied in a controlled manner.

A further feature or aspect of an embodiment is believed at the time of the filing of this patent application to possibly reside broadly in a device for the sterilization of containers with ultraviolet radiation, with a ultraviolet radiation source, the radiation from which is emitted in the interior of the container, characterized by the fact that the output of the ultraviolet source is connected with at least one optical waveguide element which can be introduced with its one end that is farther from the ultraviolet source through the container mouth into the respective container for the emission of the ultraviolet radiation.

Another feature or aspect of an embodiment is believed at the time of the filing of this patent application to possibly reside broadly in a device, characterized by the fact that the optical waveguide element is realized on the end so that it emits the ultraviolet radiation over a three-dimensional aperture angle of three hundred sixty degrees or almost three hundred sixty degrees.

Yet another feature or aspect of an embodiment is believed at the time of the filing of this patent application to possibly reside broadly in a device, characterized by the fact that the optical waveguide element is realized on the end so that it emits the ultraviolet radiation over a three-dimensional aperture angle of three hundred sixty degrees, whereby means are provided that vary the radiation output angle in a controlled manner.

Still another feature or aspect of an embodiment is believed at the time of the filing of this patent application to possibly reside broadly in a device, characterized by the fact that the optical waveguide element is flexible.

A further feature or aspect of an embodiment is believed at the time of the filing of this patent application to possibly reside broadly in a device, characterized by the fact that on a machine element, for example on a rotor that rotates around a vertical machine axis, a plurality of working positions are provided for the sterilization of one container each, and that at each working position, an optical waveguide element is provided that can be connected with a ultraviolet source and introduced into a container to be sterilized.

Another feature or aspect of an embodiment is believed at the time of the filing of this patent application to possibly reside broadly in a device, characterized by the fact that each working position has its own ultraviolet source.

Yet another feature or aspect of an embodiment is believed at the time of the filing of this patent application to possibly reside broadly in a device, characterized by the fact that a common ultraviolet source is provided on the machine element for all the working positions or an individual ultraviolet source for groups of a plurality of working positions.

Still another feature or aspect of an embodiment is believed at the time of the filing of this patent application to possibly reside broadly in a device, characterized by the fact that the optical element is realized so that the radiation emitted from said element is not uniform when viewed over the surface of the optical element.

A further feature or aspect of an embodiment is believed at the time of the filing of this patent application to possibly reside broadly in a beverage bottling plant for filling beverage bottles with liquid beverage material, said beverage bottling plant comprising: a beverage bottle cleaning machine being configured and disposed to clean beverage bottles; a feed arrangement to supply beverage bottles to said beverage bottle cleaning machine; a beverage filling machine being configured and disposed to fill beverage bottles with liquid beverage material; said beverage filling machine comprising a plurality of beverage filling elements for filling beverage bottles with liquid beverage material; at least one liquid reservoir being configured to hold a liquid to be bottled; said at least one liquid reservoir comprising a gas headspace being disposed above a liquid to be bottled within said at least one liquid reservoir; at least one supply line being configured and disposed to connect said at least one liquid reservoir to said beverage filling machine to supply liquid beverage material to said beverage filling machine; a first conveyer arrangement being configured and disposed to move beverage bottles from said beverage bottle cleaning machine into said beverage filling machine; said first conveyer arrangement comprising a star wheel structure; a beverage bottle closing machine being configured and disposed to close tops of filled beverage bottles; a second conveyer arrangement being configured and disposed to move filled beverage bottles from said beverage filling machine into said beverage bottle closing machine; said second conveyer arrangement comprising a star wheel structure; a beverage bottle labeling machine being configured and disposed to label filled, closed beverage bottles; a third conveyor arrangement being configured and disposed to move filled, closed beverage bottles from said beverage bottle closing machine into said beverage bottle labeling machine; said third conveyer arrangement comprising a star wheel structure; a beverage bottle packing station being configured and disposed to package labeled, filled, closed beverage bottles; a fourth conveyor arrangement being configured and disposed to move labeled, filled, closed beverage bottles from said beverage bottle labeling machine to said beverage bottle packing station; said fourth conveyer arrangement comprising a linear conveyor structure being configured and disposed to arrange beverage bottles in groups for packing; a computer control system being configured and disposed to monitor and control operation of said beverage bottling plant; a beverage bottle treatment machine being configured and disposed to treat bottles to be filled; said beverage bottle treatment machine comprising: a treatment device being configured and disposed to treat the insides of bottles to be filled, comprising: a source of treatment medium being configured to treat bottles; a directing apparatus being configured and disposed to direct treatment from said source to the interior of a bottle; and a movement apparatus being configured and disposed to bring said directing apparatus into a bottle to be treated and to bring said directing apparatus out of the bottle upon the bottle being treated.

Another feature or aspect of an embodiment is believed at the time of the filing of this patent application to possibly reside broadly in a treatment device being configured and disposed to treat the insides of bottles to be filled, comprising: a source of treatment medium being configured to treat bottles; a directing apparatus being configured and disposed to direct treatment from said source to the interior of a bottle; a movement apparatus being configured and disposed to bring said directing apparatus into a bottle to be treated and to bring said directing apparatus out of the bottle upon the bottle being treated.

The components disclosed in the various publications, disclosed or incorporated by reference herein, may possibly be used in possible embodiments of the present invention, as well as equivalents thereof.

Some examples of bottling systems, which may be used or adapted for use in at least one possible embodiment of the present may be found in the following U.S. patents assigned to the Assignee herein, namely: U.S. Pat. No. 4,911,285; U.S. Pat. No. 4,944,830; U.S. Pat. No. 4,950,350; U.S. Pat. No. 4,976,803; U.S. Pat. No. 4,981,547; U.S. Pat. No. 5,004,518; U.S. Pat. No. 5,017,261; U.S. Pat. No. 5,062,917; U.S. Pat. No. 5,062,918; U.S. Pat. No. 5,075,123; U.S. Pat. No. 5,078,826; U.S. Pat. No. 5,087,317; U.S. Pat. No. 5,110,402; U.S. Pat. No. 5,129,984; U.S. Pat. No. 5,167,755; U.S. Pat. No. 5,174,851; U.S. Pat. No. 5,185,053; U.S. Pat. No. 5,217,538; U.S. Pat. No. 5,227,005; U.S. Pat. No. 5,413,153; U.S. Pat. No. 5,558,138; U.S. Pat. No. 5,634,500; U.S. Pat. No. 5,713,403; U.S. Pat. No. 6,276,113; U.S. Pat. No. 6,213,169; U.S. Pat. No. 6,189,578; U.S. Pat. No. 6,192,946; U.S. Pat. No. 6,374,575; U.S. Pat. No. 6,365,054; U.S. Pat. No. 6,619,016; U.S. Pat. No. 6,474,368; U.S. Pat. No. 6,494,238; U.S. Pat. No. 6,470,922; and U.S. Pat. No. 6,463,964.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

Some examples of stepping motors that may possibly be utilized or possibly adapted for use in at least one possible embodiment of the present application may possibly be found in the following U.S. patents: U.S. Pat. No. 6,348,774 issued to Andersen et al. on Feb. 19, 2002; U.S. Pat. No. 6,373,209 issued to Gerber et al. on Apr. 16, 2002; U.S. Pat. No. 6,424,061 issued to Fukuda et al. on Jul. 23, 2002; U.S. Pat. No. 6,509,663 issued to Aoun on Jan. 21, 2003; U.S. Pat. No. 6,548,923 to Ohnishi et al. on Apr. 15, 2003; and U.S. Pat. No. 6,661,193 issued to Tsai on Dec. 9, 2003.

The appended drawings in their entirety, including all dimensions, proportions and/or shapes in at least one embodiment of the invention, are accurate and are hereby included by reference into this specification.

Some examples of servo-motors that may possibly be utilized or possibly adapted for use in at least one possible embodiment of the present application may possibly be found in the following U.S. patents: U.S. Pat. No. 4,050,434 issued to Zbikowski et al. on Sep. 27, 1977; U.S. Pat. No. 4,365,538 issued to Andoh on Dec. 28, 1982; U.S. Pat. No. 4,550,626 issued to Brouter on Nov. 5, 1985; U.S. Pat. No. 4,760,699 issued to Jacobsen et al. on Aug. 2, 1988; U.S. Pat. No. 5,076,568 issued to de Jong et al. on Dec. 31, 1991; and U.S. Pat. No. 6,025,684 issued to Yasui on Feb. 15, 2000.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

Some examples of synchronous motors which may possibly be utilized or adapted for use in at least one possible embodiment may possibly be found in the following U.S. Patents: U.S. Pat. No. 6,713,899, entitled "Linear synchronous motor;" U.S. Pat. No. 6,486,581, entitled "Interior permanent magnet synchronous motor;" U.S. Pat. No. 6,424,114, entitled "Synchronous motor;" U.S. Pat. No. 6,388,353, entitled "Elongated permanent magnet synchronous motor;" U.S. Pat. No. 6,329,728, entitled "Cylinder-type linear synchronous motor;" U.S. Pat. No. 6,025,659, entitled "Synchronous motor with movable part having permanent magnets;" U.S. Pat. No. 5,936,322, entitled "Permanent magnet type synchronous motor;" and U.S. Pat. No. 5,448,123, entitled "Electric synchronous motor."

All, or substantially all, of the components and methods of the various embodiments may be used with at least one embodiment or all of the embodiments, if more than one embodiment is described herein.

Some examples of lifting devices that may possibly be utilized or possibly adapted for use in at least one possible embodiment of the present application may possibly be found in the following patent publications: U.S. Pat. No. 2,535,272 issued to Detrez on Dec. 26, 1950; U.S. Pat. No. 2,642,214 issued to Lippold on Jun. 16, 1953; German Utility Model No. DE-GM 1,923,261 issued on Sep. 9, 1965; German Laid Open Patent Application No. DE-OS 1,532,586 published on Oct. 2, 1969; British Patent No. 1,188,888 issued Apr. 22, 1970; German Laid Open Patent Application No. DE-OS 26 52 910 published on May 24, 1978; German Patent No. DE-PS 26 52 918 issued on Oct. 26, 1978; German Utility Model No. DE-GM 83 04 995 issued on Dec. 22, 1983; German Patent No. DE-PS 26 30 100 issued on Dec. 3, 1981; and German Laid Open Patent Application No. DE-OS 195 45 080 published on Jun. 5, 1997.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

Some examples of computer systems that may possibly be utilized or possibly adapted for use in at least one possible embodiment of the present application may possibly be found in the following U.S. Patents: U.S. Pat. No. 5,416,480 issued to Roach et al. on May 16, 1995; U.S. Pat. No. 5,479,355 issued to Hyduke on Dec. 26, 1995; U.S. Pat. No. 5,481,730 issued to Brown et al. on Jan. 2, 1996; U.S. Pat. No. 5,805,094 issued to Roach et al. on Sep. 8, 1998; U.S. Pat. No. 5,881,227 issued to Atkinson et al. on Mar. 9, 1999; and U.S. Pat. No. 6,072,462 issued to Moshovich on Jun. 6, 2000.

All of the patents, patent applications and publications recited herein, and in the Declaration attached hereto, are hereby incorporated by reference as if set forth in their entirety herein.

Some examples of pneumatic arrangements that may possibly be utilized or possibly adapted for use in at least one possible embodiment of the present application may possibly be found in the following U.S. Patents: U.S. Pat. No. 6,609,767 issued to Mortenson et al. on Aug. 26, 2003; U.S. Pat. No. 6,632,072 issued to Lipscomb et al. on Oct. 14, 2003; U.S. Pat. No. 6,637,838 issued to Watanabe on Oct. 28, 2003; U.S. Pat. No. 6,659,693 issued to Perkins et al. on Dec. 9, 2003; U.S. Pat. No. 6,668,848 issued to Ladler et al. on Dec. 30, 2003; and U.S. Pat. No. 6,676,229 issued to Marra et al. on Jan, 13, 2004.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

Some examples of apparatus and methods of sterilizing or cleaning containers that may possibly be utilized or possibly adapted for use in at least one possible embodiment of the present application may possibly be found in the following U.S. Patents: U.S. Pat. No. 5,092,356 issued to Grot on Mar. 3, 1992; U.S. Pat. No. 5,320,144 issued to Ahlers on Jun. 14, 1994; U.S. Pat. No. 5,533,552 issued to Ahlers on Jul. 9, 1996; U.S. Pat. No. 5,558,135 issued to Kronseder et al. on Sep. 24, 1996; and U.S. Pat. No. 5,896,899 issued to Schlitz on Apr. 27, 1999.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

Some examples of bottling systems which may possibly be utilized or adapted for use in at least one possible embodiment may possibly be found in the following U.S. patents: U.S. Pat. No. 6,684,602, entitled "Compact bottling machine;" U.S. Pat. No. 6,470,922, entitled "Bottling plant for bottling carbonated beverages;" U.S. Pat. No. 6,390,150, entitled "Drive for bottling machine;" U.S. Pat. No. 6,374,575, entitled "Bottling plant and method of operating a bottling plant;" U.S. Pat. No. 6,192,946, entitled "Bottling system;" U.S. Pat. No.

6,185,910, entitled "Method and an apparatus for high-purity bottling of beverages;" U.S. Pat. No. 6,058,985, entitled "Bottling machine with a set-up table and a set-up table for a bottling machine and a set-up table for a bottle handling machine;" U.S. Pat. No. 5,996,322, entitled "In-line bottling plant;" U.S. Pat. No. 5,896,899, entitled "Method and an apparatus for sterile bottling of beverages;" U.S. Pat. No. 5,848,515, entitled "Continuous-cycle sterile bottling plant;" U.S. Pat. No. 5,634,500, entitled "Method for bottling a liquid in bottles or similar containers;" and U.S. Pat. No. 5,425,402, entitled "Bottling system with mass filling and capping arrays."

The corresponding foreign patent publication applications, namely, Federal Republic of Germany Patent Application No. 10 2004 032 861.7, filed on Jul. 7, 2004, having inventor Volker Till, and DE-OS 10 2004 032 861.7 and DE-PS 10 2004 032 861.7, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

Some examples of starwheels which may possibly be utilized or adapted for use in at least one possible embodiment may possibly be found in the following U.S. Patents: U.S. Pat. No. 5,613,593, entitled "Container handling starwheel;" U.S. Pat. No. 5,029,695, entitled "Improved starwheel;" U.S. Pat. No. 4,124,112, entitled "Odd-shaped container indexing starwheel;" and U.S. Pat. No. 4,084,686, entitled "Starwheel control in a system for conveying containers."

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

Some examples of heaters or heat exchangers, cooling systems, valves, pumps, or tanks that may be used or adapted for use in at least one possible embodiment of the present invention may be found in the following U.S. patents: U.S. Pat. No. 5,881,952, issued to inventor Macintyre on Mar. 16, 1999; U.S. Pat. No. 5,862,669, issued to inventors Davis et al. on Jan. 26, 1999; U.S. Pat. No. 5,459,890, issued to inventor Jarocki on Oct. 24, 1995; U.S. Pat. No. 5,367,602, issued to inventor Stewart on Nov. 22, 1994; U.S. Pat. No. 5,319,973, issued to inventors Crayton et al. on Jun. 14, 1994; U.S. Pat. No. 5,226,320, issued to inventors Dages et al. on Jul. 13, 1993; U.S. Pat. No. 5,078,123, issued to inventors Nagashima et al. on Jan. 7, 1992; and U.S. Pat. No. 5,068,030, issued to inventor Chen on Nov. 26, 1991.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72 (b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A method of operating a bottling plant, said method comprising the steps of:

moving bottles to be filled into a rotary bottle sterilizing arrangement and sterilizing at least two of the bottles simultaneously in said rotary bottle sterilizing arrangement;

said step of sterilizing each of the bottles comprising:

providing ultraviolet light and emitting said ultraviolet light from an emitting device;

positioning said emitting device inside the bottle;

emitting said ultraviolet light from said emitting device in a spherical pattern and sterilizing the inside surface of the bottle, wherein the intensity of the ultraviolet radiation that is emitted in a spherical pattern is not distributed uniformly over the surface of an imaginary sphere, and irradiating predetermined areas of the bottles more intensively than other areas of the bottles; and positioning said emitting device outside the bottle upon completion of treatment of the inside surface of the bottle with ultraviolet light;

moving the sterilized bottles out of said bottle sterilizing arrangement and into a rotary bottle filling arrangement;

filling the sterilized bottles with a liquid product;

moving the filled bottles out of said bottle filling arrangement and into a bottle closing arrangement;
closing the tops of filled bottles; and
moving the closed bottles out of said bottle closing arrangement.

2. The method according to claim 1, wherein said emitting devices are flexible.

3. The method according to claim 2, wherein:
said step of positioning said emitting device inside the bottle comprises one of:
moving the bottle relative to said emitting device to thereby position said emitting device inside the bottle; and
moving said emitting device relative to the bottle to thereby position said emitting device inside the bottle; and
said step of positioning said emitting device outside the bottle comprises one of:
moving the bottle relative to said emitting device to thereby position said emitting device outside the bottle; and
moving said emitting device relative to the bottle to thereby position said emitting device outside the bottle.

4. The method according to claim 3, wherein:
said emitting device comprises optical fibers configured to emit ultraviolet light;
said rotary bottle sterilizing arrangement comprises:
a rotor configured and disposed to rotate about a central vertical axis; and
a plurality of bottle holders disposed about and on the periphery of said rotor;
each of said emitting devices is disposed at a corresponding one of said bottle holders; and
said rotary bottle sterilizing arrangement comprises a plurality of ultraviolet sources configured and disposed to supply ultraviolet light to a corresponding one of said emitting devices.

5. The method according to claim 3, wherein:
said emitting device comprises optical fibers configured to emit ultraviolet light;
said rotary bottle sterilizing arrangement comprises:
a rotor configured and disposed to rotate about a central vertical axis; and
a plurality of bottle holders disposed about and on the periphery of said rotor;
each of said emitting devices is disposed at a corresponding one of said bottle holders; and
said rotary bottle sterilizing arrangement comprises a common ultraviolet source configured and disposed to supply ultraviolet light to all of said emitting devices.

* * * * *